(12) United States Patent
Barker

(10) Patent No.: US 11,412,999 B2
(45) Date of Patent: Aug. 16, 2022

(54) METHODS AND SYSTEMS FOR A MEDICAL IMAGING SYSTEM WITH C-ARM

(71) Applicant: GE Precision Healthcare LLC, Milwaukee, WI (US)

(72) Inventor: David Barker, Salt Lake City, UT (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 165 days.

(21) Appl. No.: 16/690,051

(22) Filed: Nov. 20, 2019

(65) Prior Publication Data

US 2021/0145383 A1 May 20, 2021

(51) Int. Cl.
*G21K 4/00* (2006.01)
*A61B 6/00* (2006.01)
*D01F 9/12* (2006.01)

(52) U.S. Cl.
CPC .............. *A61B 6/4441* (2013.01); *D01F 9/12* (2013.01)

(58) Field of Classification Search
CPC ....... A61B 6/4441; A61B 34/20; A61B 90/36; A61B 2034/2072; A61B 1/00128; A61B 1/00137; A61B 1/0014; A61B 1/00147; A61B 1/0052; A61B 1/012; A61B 1/018; A61B 1/2676; A61B 2034/107; A61B 2034/2051; A61B 2034/2055; A61B 2034/256; A61B 2090/3983; A61B 90/50; A61B 90/53; A61B 90/57; A61B 6/0421; A61B 6/0487; A61B 6/06; A61B 6/08; A61B 6/405; A61B 6/482; A61B 6/488; A61B 6/505; A61B 6/548; A61B 6/583; A61B 46/00; A61B 46/10; A61B 6/4488; A61B 6/447; A61B 6/40; A61B 6/4423; A61B 6/4405; A61B 6/4233; A61B 6/035; A61B 6/4452; A61B 6/588; A61B 17/1735; A61B 17/1757; A61B 17/7089; A61B 17/8872; A61B 90/10; A61B 90/39; D01F 9/12; G06K 9/00; A61L 2/07; A61L 2/081; A61L 2/26; G21K 1/10; H05G 1/06; H05G 1/10; H05G 1/025; H05G 1/04; A61N 2005/1041; A61N 5/1081; G16H 30/20; G16H 70/20
USPC ........................................................ 378/193
See application file for complete search history.

(56) References Cited

U.S. PATENT DOCUMENTS

| | | | |
|---|---|---|---|
| 5,426,683 A * | 6/1995 | O'Farrell, Jr. ........ | A61B 6/4405 378/193 |
| 6,132,087 A * | 10/2000 | Kusch .................. | A61B 6/4405 378/197 |
| 7,543,986 B2 | 6/2009 | Saffer | |
| 10,299,747 B2 | 5/2019 | Baumann et al. | |

(Continued)

FOREIGN PATENT DOCUMENTS

| CN | 201356561 Y | 12/2009 |
|---|---|---|
| DE | 202011107140 U1 | 5/2012 |

*Primary Examiner* — Irakli Kiknadze

(57) ABSTRACT

Various methods and systems are provided for a medical imaging system C-arm. In one embodiment, an imaging system comprises a C-arm including an inner circumferential wall forming a first pair of grooved flanges and the outer circumferential wall forming a second pair of grooved flanges, where each of the first pair of grooved flanges and second pair of grooved flanges comprises a composite material. A C-shaped portion of the C-arm may be configured to rotate isocentrically around a rotational axis.

19 Claims, 8 Drawing Sheets

(56) References Cited

U.S. PATENT DOCUMENTS

| | | | |
|---|---|---|---|
| 2010/0111259 A1* | 5/2010 | Van Der Ende | H05G 1/025 |
| | | | 378/142 |
| 2015/0196262 A1 | 7/2015 | Grady | |
| 2017/0035377 A1* | 2/2017 | Grady | A61B 6/4405 |
| 2019/0008470 A1* | 1/2019 | Dirauf | A61B 6/035 |
| 2020/0054297 A1* | 2/2020 | Martinez Ferreira | |
| | | | A61B 6/4458 |

* cited by examiner

METHODS AND SYSTEMS FOR A MEDICAL IMAGING SYSTEM WITH C-ARM

FIELD

Embodiments of the subject matter disclosed herein relate to medical imaging systems, and more particularly, to radiographic imaging systems.

BACKGROUND

Radiographic imaging systems may be used in various applications, including medical and industrial applications. In a medical environment, a radiographic imaging device may provide a non-invasive means of imaging tissue and bone of a patient. The imaging device may have the capability of capturing multiple images at designated intervals, and displaying the images in a sequence to create a single image of the object being examined.

The imaging device may comprise a C-arm coupled to a base unit. The C-arm may include an x-ray source positioned at one end of the arm, and a detector positioned at another end of the arm. A clearance may be provided between the x-ray source and detector to receive an object, such as a portion of the patient's body, which may be irradiated with radiation from the x-ray source. Upon irradiating the object, the x-ray radiation penetrates the object, before being captured by the detector on the other end of the object. By penetrating the object placed between the source and detector, the x-rays enable an image of the object to be captured and relayed to the display monitor, where the image may be displayed or stored and retrieved later.

BRIEF DESCRIPTION

In one embodiment, an imaging system comprises a C-arm including an inner circumferential wall forming a first pair of grooved flanges and the outer circumferential wall forming a second pair of grooved flanges, where each of the first pair of grooved flanges and second pair of grooved flanges comprises a composite material.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIGS. 5-8 are shown to scale, though other relative dimensions may be used, if desired.

DETAILED DESCRIPTION

Figure 2:
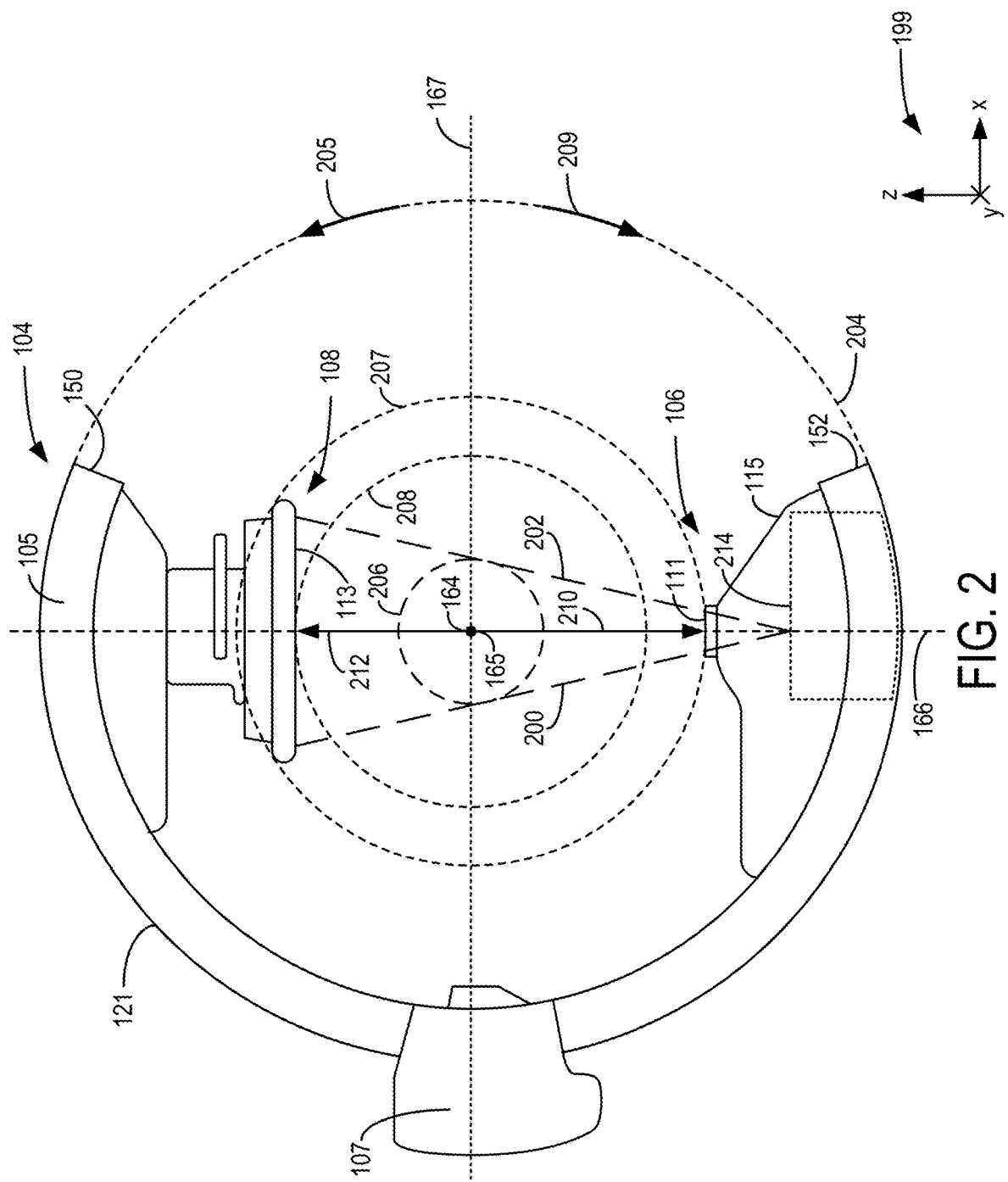
FIG. 2 is a partial view of the C-arm of FIG. 1 in a first position.
Figure 4:
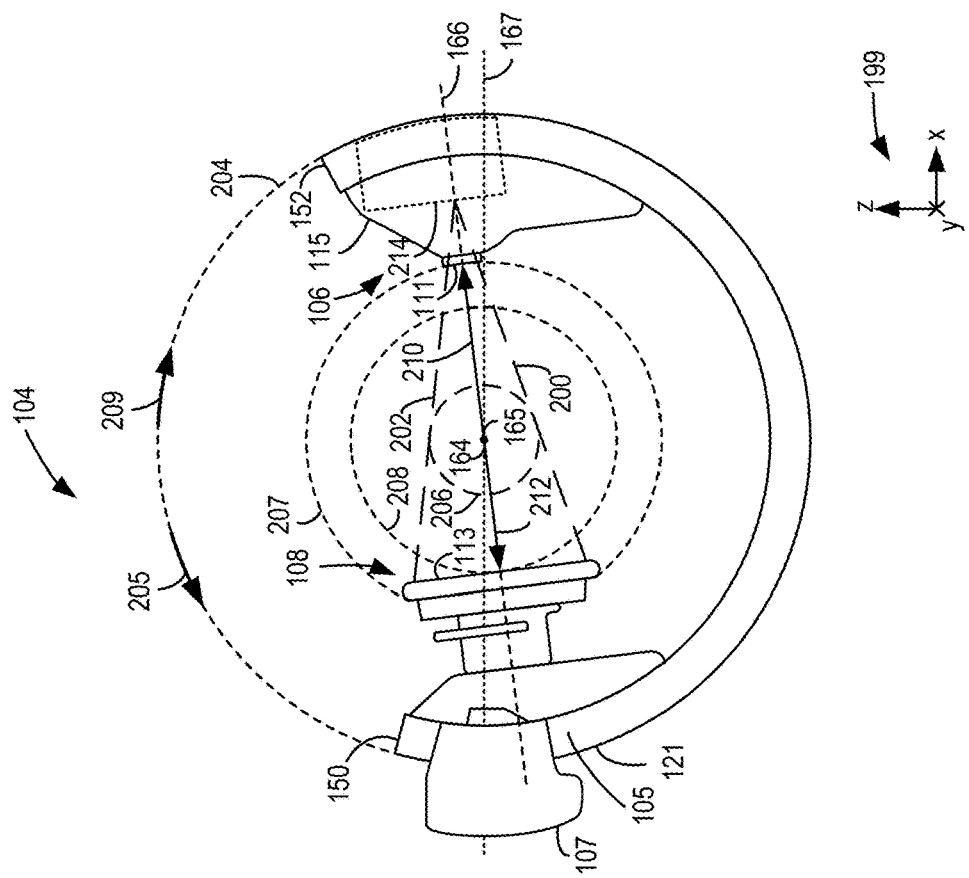
FIG. 4 is a partial view of the C-arm of FIGS. 1-3 in a third position.
Figure 3:
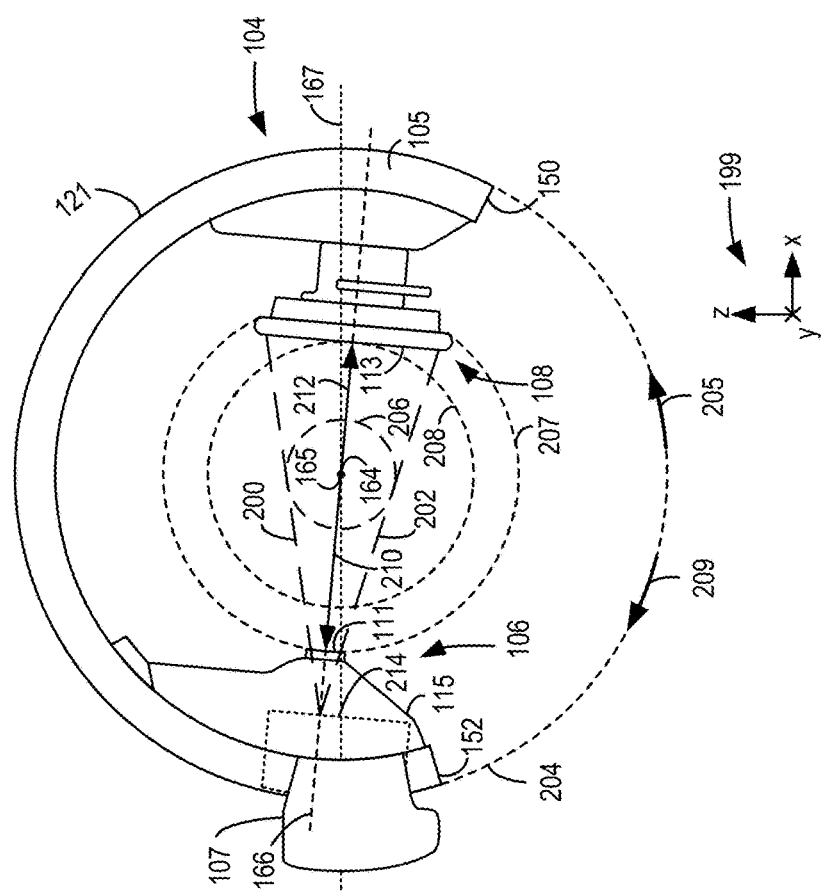
FIG. 3 is a partial view of the C-arm of FIGS. 1-2 in a second position.
Figure 5:
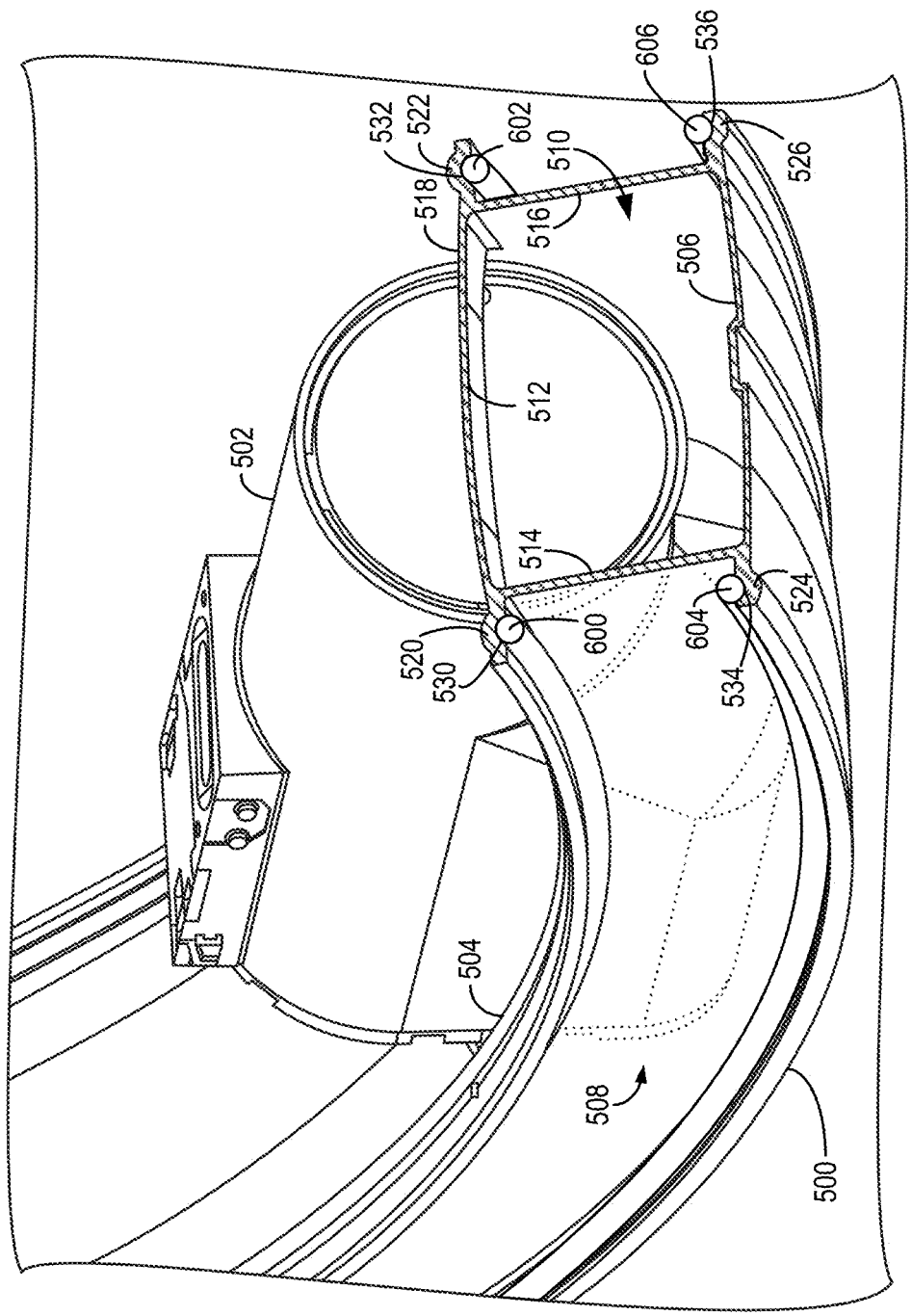
FIG. 5 is a perspective view of a C-shaped portion of a C-arm housing a radiation source.
Figure 6:
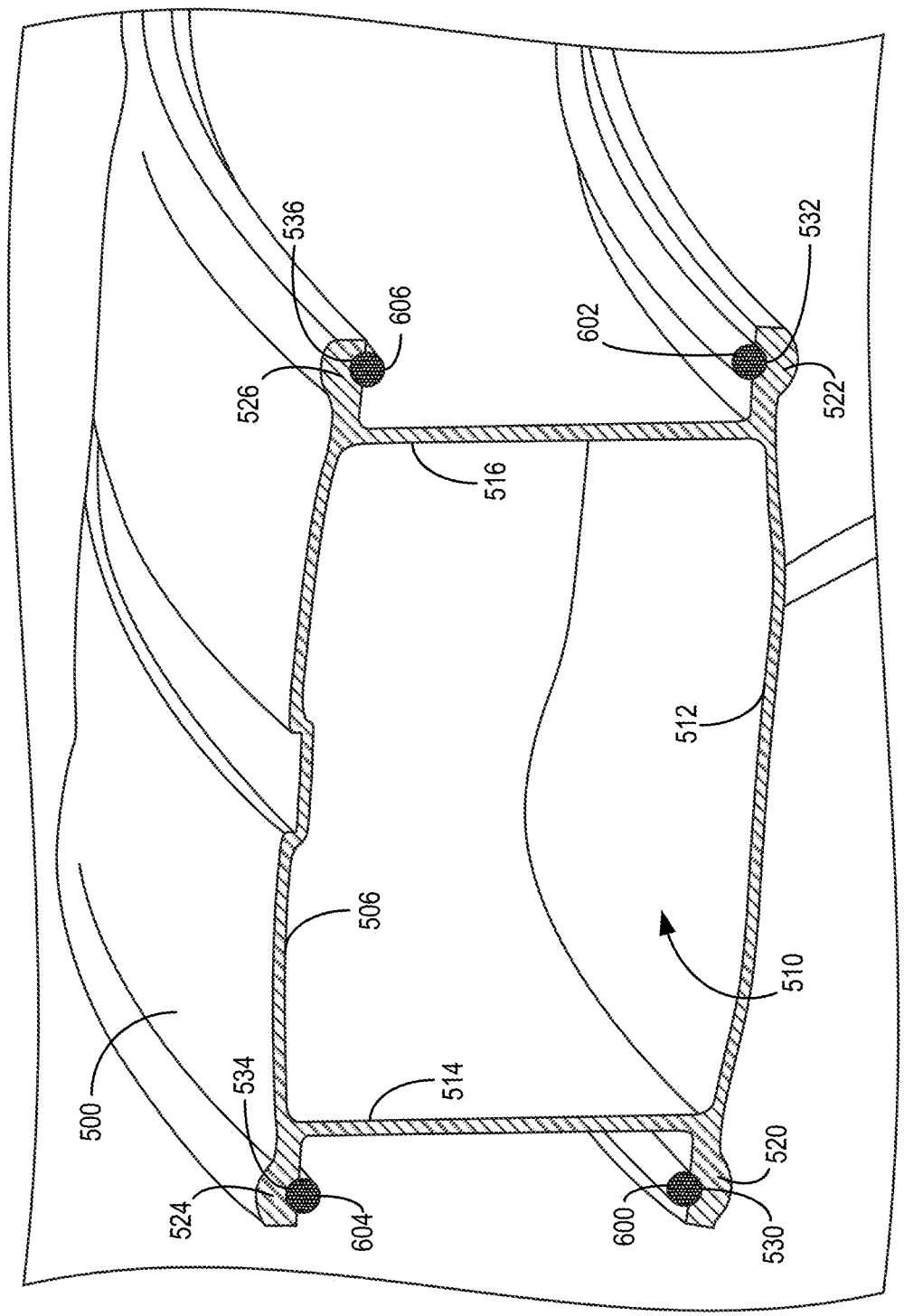
FIG. 6 is perspective view of the C-shaped portion of FIG. 5, with annular rods positioned at respective grooved flanges of the C-shaped portion.
Figure 7:
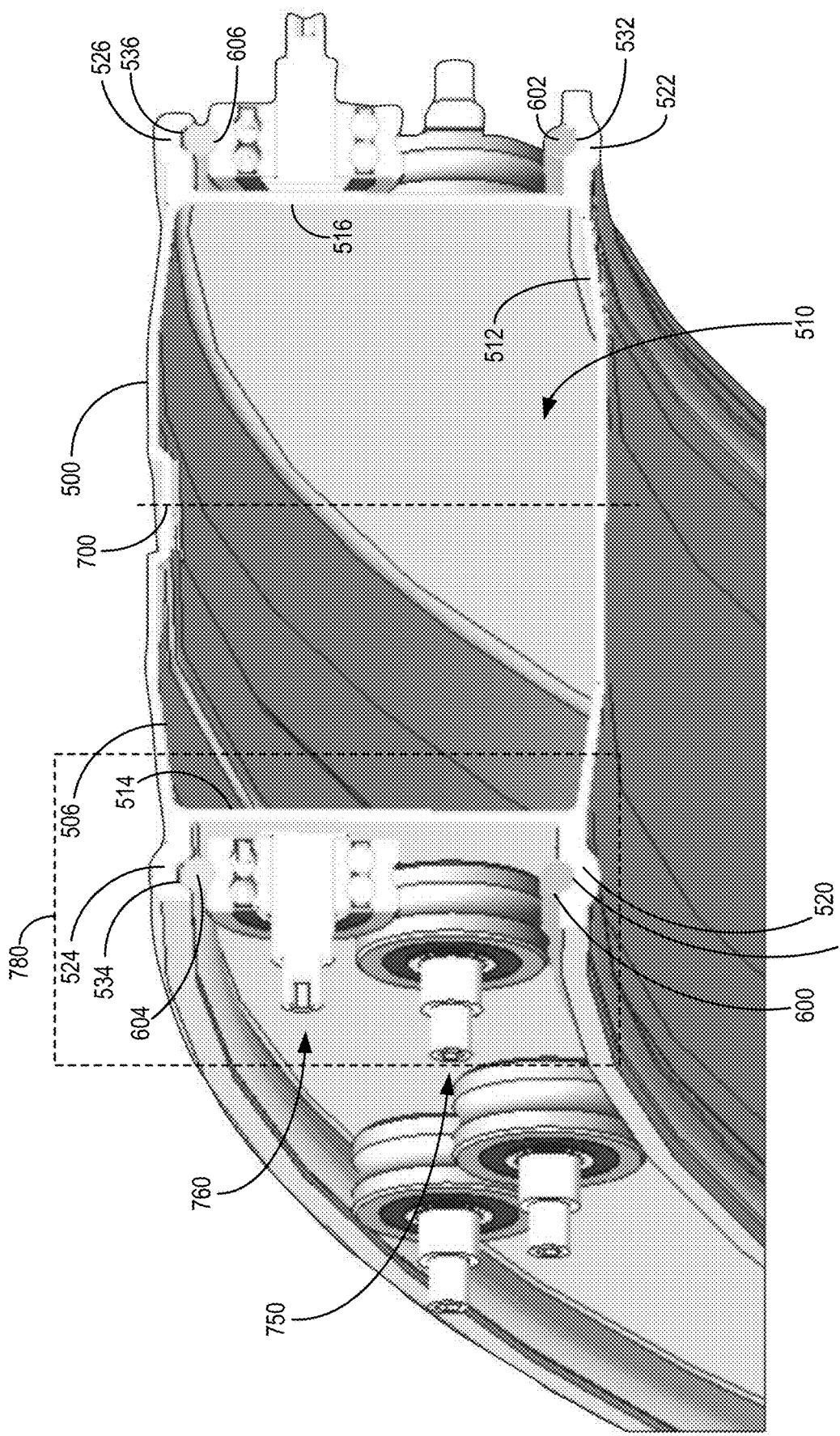
FIG. 7 shows a perspective view of the C-shaped portion of FIGS. 5-6, with the annular rods engaged with grooved rollers.
Figure 8:
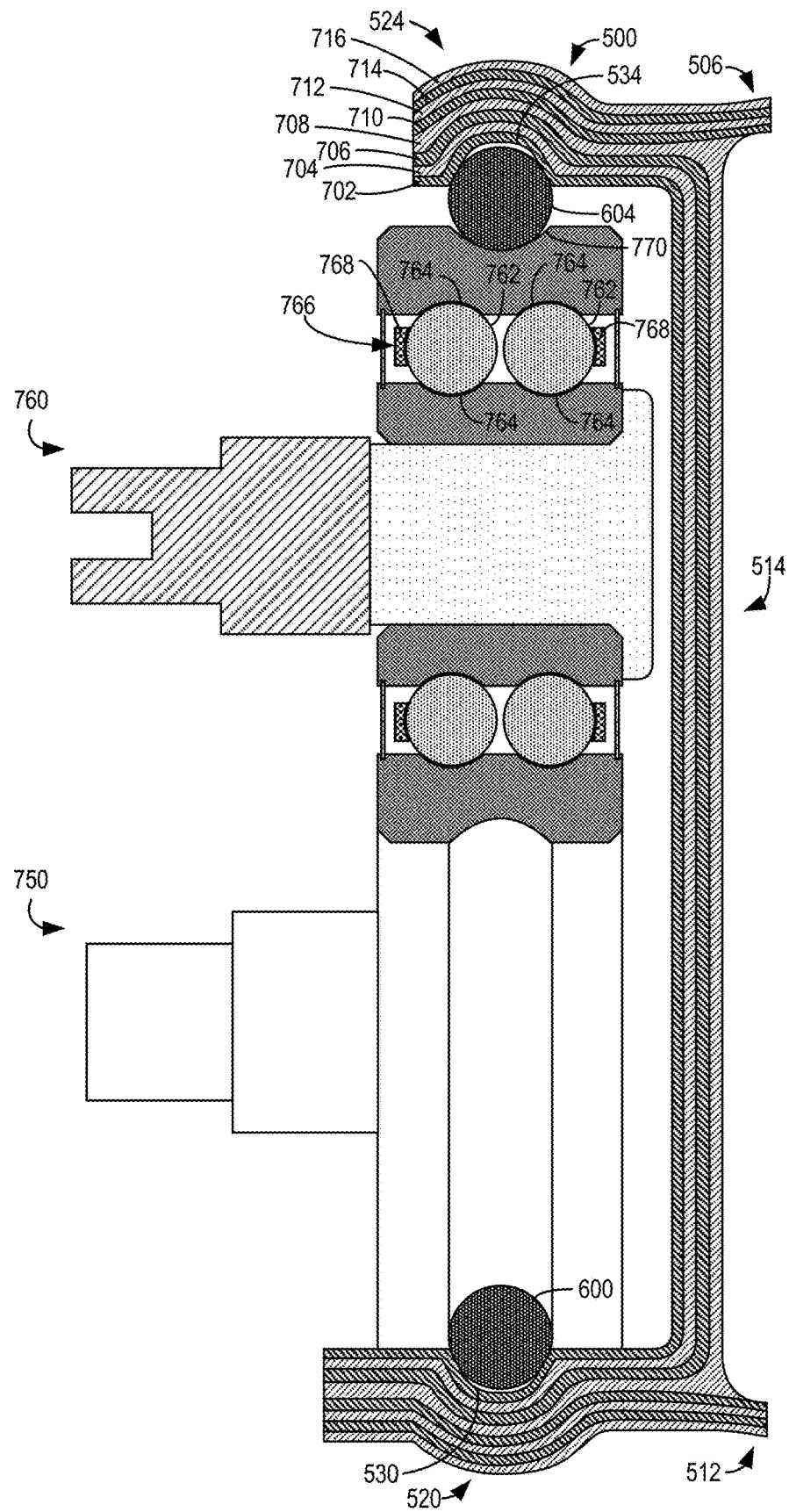
FIG. 8 is a side cross-sectional view of the C-shaped portion of FIGS. 5-7, with the annular rods positioned at the respective grooved flanges.
Figure 9:
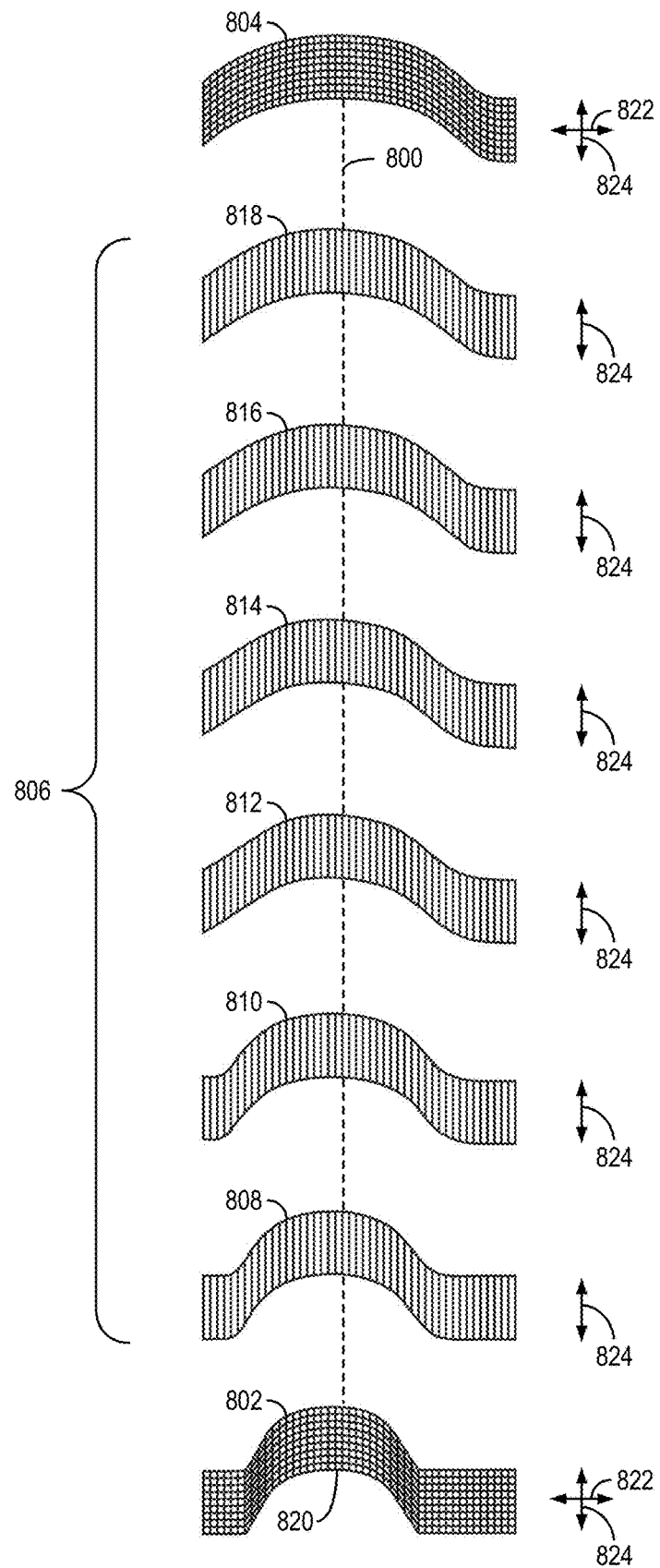
FIG. 9 is an exploded view of a plurality of layers of composite material forming a grooved flange of a C-shaped portion of a C-arm.

The following description relates to various embodiments for an imaging system including a C-arm. An imaging system, such as the imaging system shown by FIG. 1, includes a C-arm configured to rotate around at least one rotational axis. The C-arm includes an x-ray source and an x-ray detector arranged at opposite ends of a C-shaped portion, where a subject to be imaged may be positioned in an imaging area between the x-ray source and x-ray detector. The C-shaped portion may rotate isocentrically, as shown by FIGS. 2-4, with the x-ray source seated within an interior clearance of the C-shaped portion, as shown by FIG. 5. The C-shaped portion may include a plurality of grooved flanges, as shown by FIG. 6, with the grooved flanges configured to engage with respective annular rods. The annular rods form an interface between the grooved flanges and bearing assemblies of the imaging system, as shown by FIGS. 7-8, for rotation of the C-shaped portion. The grooved flanges may be formed of a composite material comprising external layers and a plurality of intermediate layers, as shown by FIG. 9. The layers of composite material may include exterior layers with fibers oriented perpendicular to each other and intermediate layers with fibers oriented only parallel to each other. The layers may additional form one or more walls of the C-shaped portion to further increase a strength of the C-shaped portion and/or reduce a load of the imaging system.

Figure 1:
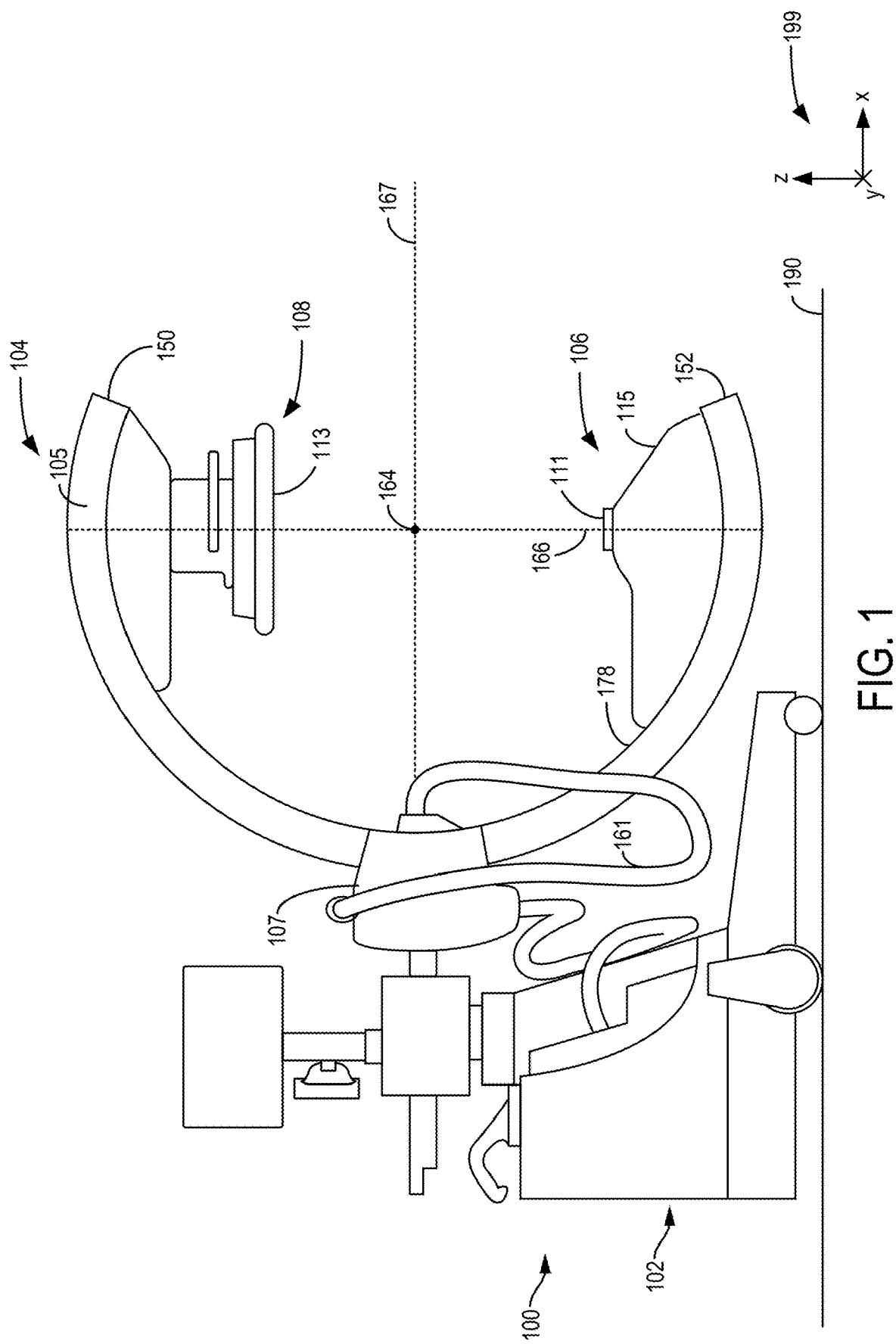
FIG. 1 is a side view of a medical imaging system including a C-arm, according to an embodiment.

Turning to FIG. 1, a side view of an imaging system 100 is shown, where the imaging system includes C-arm 104 with a radiation source. In the examples described herein, the radiation source is an x-ray source 106 positioned opposite to x-ray detector 108. However, in other examples, the radiation source may be configured to emit a different type of radiation for imaging (e.g., imaging a patient), such as gamma rays, and the detector (e.g., x-ray detector 108) may be configured to detect the radiation emitted by the radiation source. The imaging system 100 additionally includes base unit 102 supporting imaging system 100 on ground surface 190 on which the imaging system 100 sits.

The C-arm 104 includes a C-shaped portion 105 connected to an extended portion 107, with the extended portion 107 rotatably coupled to the base unit 102. As an example, the C-arm 104 may be configured to rotate at least 180 degrees in opposing directions relative to the base unit 102. The C-arm 104 is rotatable about at least a rotational axis 164. The C-shaped portion 105 may be rotated as described above in order to adjust the x-ray source 106 and detector 108 (positioned on opposite ends of the C-shaped portion of the C-arm 104 along axis 166, where axis 166 intersects rotational axis 164 and extends radially relative to rotational axis 164) through a plurality of positions.

During an imaging operation, a portion of a patient's body placed in a clearance (e.g., gap) formed between the x-ray source 106 and detector 108, may be irradiated with radiation from the x-ray source. For example, x-ray source 106 may comprise an x-ray tube housed within casing 115, and x-ray radiation generated by the x-ray source 106 may emit from an outlet 111 of the casing 115 and may be intercepted by a detector surface 113 of the detector 108. The radiation may penetrate the portion of the patient's body being irradiated, and travel to the detector 108 where the radiation is captured. By penetrating the portion of the patient's body placed between the x-ray source 106 and detector 108, an image of the patient's body is captured and relayed to an electronic controller of the imaging system 100 (e.g., via an electrical connection line, such as electrically conductive cable 161).

The base unit 102 may include the electronic controller (e.g., a control and computing unit) that processes instructions or commands sent from the user input devices during operation of the imaging system 100. The base unit 102 may also include an internal power source (not shown) that provides electrical power to operate the imaging system 100. Alternatively, the base unit 102 may be connected to an external electrical power source to power the imaging system 100. A plurality of connection lines (e.g., electrical cables, such as electrically conductive cable 161) may be provided to transmit electrical power, instructions, and/or data between the x-ray source 106, detector 108, and the control and computing unit. The plurality of connection lines may transmit electrical power from the electrical power source (e.g., internal and/or external source) to the x-ray source 106 and detector 108.

The C-arm 104 may be adjusted to a plurality of different positions by rotation of the C-shaped portion 105 of the C-arm 104. For example, in an initial, first position shown by FIG. 1, the detector 108 may be positioned vertically above the x-ray source 106 relative to a ground surface 190 on which the imaging system 100 sits, with axis 166 arranged normal to the ground surface 190 intersecting a midpoint of each of the outlet 111 of x-ray source 106 and detector surface 113 of detector 108. The C-arm 104 may be adjusted from the first position to a different, second position by rotating the C-shaped portion 105. In one example, the second position may be a position in which the x-ray source 106 and detector 108 are rotated 180 degrees together relative to the first position, such that the x-ray source 106 is positioned vertically above the detector 108, with axis 166 intersecting the midpoint of the outlet 111 of the x-ray source 106 and the midpoint of the detector surface 113 of the detector 108. When adjusted to the second position, the x-ray source 106 may be positioned vertically above the rotational axis 164 of the C-shaped portion 105 of the C-arm 104, and the detector 108 may be positioned vertically below the rotational axis 164. Different example positions of the C-arm 104 rotated via the coupling between the extended portion 107 and C-shaped portion 105 are shown by FIGS. 2-4 and described further below.

As described above, the imaging system 100 includes x-ray source 106 positioned across rotational axis 164 relative to the detector 108. In the example shown by FIG. 1, detector 108 is positioned at a first end 150 of the C-shaped portion, and x-ray source 106 is positioned at an opposing, second end 152 of the x-ray source 106. In some examples, similar to those described further below, the C-shaped portion 105 includes an opening shaped to receive a casing of the x-ray source 106. The x-ray source 106 may comprise an x-ray tube (e.g., a vacuum tube configured to produce x-ray radiation) housed within the casing, and the x-ray tube may be seated within a clearance formed between opposing walls of the C-shaped portion 105 through the opening.

By arranging the x-ray tube to be positioned within the clearance of the C-shaped portion 105, a height of the x-ray source 106 (e.g., a length of the x-ray source 106 along axis 166 from the outlet 111 of the x-ray source 106 to the detector surface 113 of detector 108) may be reduced. The reduced height of the x-ray source 106 may increase an amount of open space between the detector surface 113 and the outlet 111 of the x-ray source 106, which may enable the C-arm 104 to accommodate larger patients for imaging and/or increase an ease of use of the C-arm 104 (e.g., increase an operating clearance of the C-arm 104) while maintaining the rotational axis 164 at the centered position between the first end 150 and the second end 152 (e.g., maintaining the rotational axis 164 an equal distance from each of the first end 150 and the second end 152 in the direction of axis 166). Maintaining the rotational axis 164 at the centered position may reduce a load (e.g., torque) on the C-shaped portion 105 during conditions in which the C-shaped portion 105 is rotated around the rotational axis 164 by reducing an eccentric motion of the C-shaped portion 105 relative to C-arms that do not include the rotational axis 164 at the centered position. As a result, a durability of the C-arm 104 may be increased and a likelihood of degradation of the C-arm 104 may be reduced.

In some examples, the C-shaped portion 105 of the C-arm 104 may be formed from a composite material, such as carbon fiber fabric. In one example, as described further below, the C-shaped portion 105 includes a plurality of grooved flanges, with each grooved flange formed from the composite material. The grooved flanges may couple the C-arm 104 to the base unit 102 via an interface between the grooved flanges and the extended portion 107. In examples in which the composite material is carbon fiber fabric, the grooved flanges may be formed through layering of a plurality of layers of the carbon fiber fabric, with one or more layers having a different carbon fiber orientation relative to other layers. Due to a strength of the carbon fiber fabric (e.g., a rigidity and/or load potential), the grooved flanges may maintain the C-shaped portion 105 of the C-arm 104 in engagement with the extended portion 107 while also decreasing the weight of the C-shaped portion 105 relative to C-arms that do not include grooved flanges formed from the composite material. Further, in some examples, the weight of the C-shaped portion 105 may be further reduced by forming one or more walls of the C-shaped portion 105 from the composite material. By forming the grooved flanges and/or walls of the C-shaped portion 105 from the composite material, the weight of the C-shaped portion 105 may be reduced and a load on the imaging system may be decreased (e.g., a load on a motor of the imaging system configured to rotate the C-shaped portion 105 around the rotational axis 164).

Referring collectively to FIGS. 2-4, various example positions of the C-shaped portion 105 are shown. Specifically, FIG. 2 shows the C-shaped portion 105 in a first position in which the axis 166 between the detector surface 113 and the outlet 111 of the x-ray source 106 is arranged perpendicular to the ground surface 190 on which the imaging system 100 sits (shown by FIG. 1, with axis 167 being an axis parallel to the ground surface 190 and perpendicular to a direction of gravity and rotational axis 164). FIG. 3 shows the C-shaped portion 105 in a first rotated position in which the x-ray source 106 is positioned closer to extended portion 107 and detector 108 is positioned further from extended portion 107 relative to the first position shown by FIG. 2, and FIG. 4 shows the C-shaped portion 105 in a second rotation position in which the detector 108 is positioned closer to the extended portion 107 and the x-ray source 106 is positioned further from the extended portion 107 relative to the first position. Cable 161 shown by FIG. 1 is omitted from FIGS. 2-4 for illustrative clarity. A rotational range of the C-shaped portion 105 (e.g., an amount of angle through which the C-shaped portion 105 may rotate relative to the base unit 102) may be greater than 180 degrees. As one example, FIG. 3 may correspond to a rotation of the C-shaped portion 105 by an angle of 95 degrees around the rotational axis 164 relative to the position shown by FIG. 2, and FIG. 4 may correspond to a rotation of the C-arm 104 by an angle of −95 degrees around the rotational axis 164 relative to the position shown by FIG. 2, with the C-shaped portion 105 rotating through 190 degrees to adjust from the position shown by FIG. 4 to the position shown by FIG. 3. In each of FIGS. 2-4, the extended portion 107 is maintained in position (e.g., not rotated) relative to the C-shaped portion 105, with the position of extended portion 107 in FIGS. 2-4 being the same as the position of extended portion 107 shown in FIG. 1 (e.g., with the extended portion 107 not rotated relative to the ground surface 190 or axis 167).

Each of FIGS. 2-4 show axis 200 and axis 202 illustrating a radiation emission pathway of the x-ray source 106. Specifically, the x-ray source 106 may emit a beam of x-ray radiation between the axis 200 and axis 202, where axis 200 and axis 202 represent rays of the beam directed toward detector surface 113. As the C-shaped portion 105 rotates around the rotational axis 164 (e.g., for imaging of a patient or object to be imaged that is positioned at the rotational axis 164), the beam of x-ray radiation remains directed toward the detector surface 113 due to the concurrent rotation of each of the detector 108 and x-ray source 106 around the rotational axis 164. While rotating isocentrically around the rotational axis 164, the C-shaped portion 105 may move along rotation pathway 204 (e.g., in isocentric rotation direction 205 or opposing isocentric rotation direction 209), and because the x-ray source 106 and detector 108 rotate around the rotational axis 164 along with the C-shaped portion 105, the beam of x-ray radiation emitted by the x-ray source 106 forms an isocentric imaging area 206 of the imaging system 100 (shown by FIG. 1, the imaging system 100 including C-arm 104).

An isocenter 165 of the C-arm 104 is positioned at the rotational axis 164. Specifically, the isocenter 165 of the C-arm 104 is positioned at an intersection of rotational axis 164 and axis 167. Each of the first end 150 and second end 152 may be positioned a same length from the isocenter 165. For example, an outer surface 121 of the C-shaped portion 105 may have a uniform radius of curvature in a direction around the rotational axis 164 (e.g., a same radius of curvature at each location along the outer surface 121 in the direction around the rotational axis 164, with the isocenter 165 being the center of curvature) such that each portion of the outer surface 121, including portions positioned at the first end 150 and second end 152, is positioned a same distance from the isocenter 165 along axis 166 (e.g., as indicated by rotation pathway 204 having a same radius of curvature as the outer surface 121). As described above, the C-shaped portion 105 may rotate around the rotational axis 164 (e.g., via the coupling between the C-shaped portion 105 and the extended portion 107). In some examples, C-shaped portion 105 may also rotate around axis 167. In this con-figuration, the C-shaped portion 105 may rotate around either of rotational axis 164 or axis 167 (or both of rotational axis 164 and axis 167), where axis 167 is orthogonal to the rotational axis 164. In the views shown by FIGS. 2-4, however, the C-shaped portion 105 is rotated only around the rotational axis 164 and not the axis 167.

Although the first end 150 and second end 152 may be positioned the same length from the isocenter 165, each of detector surface 113 and outlet 111 may be positioned different lengths from the isocenter 165. For example, FIGS. 2-4 show a rotation pathway 207 of the outlet 111 and a rotation pathway 208 of the detector surface 113, with each of the rotation pathway 207 and rotation pathway 208 being of circular shape. Outlet 111 may move along rotation pathway 207 and detector surface 113 may move along rotation pathway 208 during conditions in which the C-shaped portion 105 is rotated around rotational axis 164. However, a length 212 (e.g., a diameter of the rotation pathway 208) from the isocenter 165 to the detector surface 113 may be smaller than a length 210 (e.g., a diameter of the rotation pathway 207) from the isocenter 165 to the outlet 111. As one example, the length 210 may be larger than the length 212 due to the x-ray source 106 being seated within a portion of the C-shaped portion 105. For example, x-ray tube 214 is shown schematically and illustrated by dashed lines in FIGS. 2-4 to indicate that the x-ray tube 214 is housed within casing 115 and seated within a portion of the C-shaped portion 105.

The seated position of the x-ray tube 214 within the C-shaped portion 105 may enable the outlet 111 to be positioned closer to the second end 152 compared to con-figurations in which the x-ray tube is not seated within the C-shaped portion, which may result in a decreased height of the x-ray source 106 (e.g., a decreased height of casing 115 of the x-ray tube 214). As described above, the resulting reduced height of the x-ray source 106 may increase the amount of open space between the detector surface 113 and outlet 111 (e.g., increase the length 210 between the isocenter 165 and the outlet 111 relative to the length 212 between the isocenter 165 and the detector surface 113), which may enable the C-arm 104 to accommodate larger patients and/or increase ease of use of the C-arm 104.

Further, in some examples, the seated position of the x-ray source 106 within the C-shaped portion 105 may increase a balance of the C-arm 104, which may reduce a likelihood of undesired vibration of the C-arm 104. For example, in some embodiments, the C-shaped portion 105 may be formed of a composite material, such as carbon fiber fabric. The carbon fiber fabric may provide increased strength to the C-shaped portion 105 and/or a reduced weight of the C-shaped portion 105 relative to C-arms that include a C-shaped portion formed of a different material (e.g., steel, aluminum, etc.). However, due to the reduced weight of the C-shaped portion 105 resulting from the composite material, balance characteristics of the C-shaped portion 105 may be different compared to C-shaped portions formed from other materials such as metal. By seating the x-ray source 106 within the C-shaped portion 105 formed of the composite material, the balance characteristics of the C-shaped portion 105 may be increased.

Further, in some examples, the seated position of the x-ray source 106 within the C-shaped portion 105 may increase the balance of the C-arm 104 during isocentric rotation (e.g., symmetric rotation around the isocenter 165, as described above). As one example, the seated position of the x-ray source 106 may provide counterweight to a weight of the detector 108, such that a load and/or vibration of a motor of the imaging system driving the rotation of the C-arm 104 is reduced compared to configurations that do not include the x-ray source 106 seated within the C-shaped portion 105.

Referring now to FIG. 5, a perspective view of a portion of a C-shaped portion 500 of a C-arm of an imaging system is shown. In one example, the C-shaped portion 500 may be the C-shaped portion 105 described above with reference to FIGS. 1-4. The C-shaped portion 500 includes an opening 504 shaped to receive x-ray tube 502, where the x-ray tube 502 may be housed within a casing (e.g., casing 115 described above), and the casing may be seated within the C-shaped portion 500 against an outer circumferential wall 506 (e.g., as illustrated by broken lines 508 indicating a position of the x-ray tube 502 within an interior clearance 510 of the C-shaped portion 500). In some examples, the x-ray tube 502 may be the x-ray tube 214 described above with reference to FIGS. 2-4. In some examples, the x-ray tube 502 may be seated directly against the outer circumferential wall 506 and positioned within the interior clearance 510. The x-ray tube 502 may be positioned entirely within the interior clearance 510 in some examples. Further, in some examples, an entirety of the casing may be positioned external to the interior clearance 510.

The interior clearance 510 of the C-shaped portion 500 is a hollow portion of the C-shaped portion 500 formed by each of the outer circumferential wall 506, inner circumferential wall 512, first sidewall 514, and second sidewall 516. The first sidewall 514 and second sidewall 516 join the inner circumferential wall 512 with the outer circumferential wall 506, and in some examples, the outer circumferential wall 506, inner circumferential wall 512, first sidewall 514, and second sidewall 516 may be formed together from multiple layers of composite material, as described further below. The opening 504 is formed through the inner circumferential wall 512 from an exterior surface 518 of the inner circumferential wall 512 to the interior clearance 510. In some examples, the interior clearance 510 may extend an entire length of the C-shaped portion 500 from a first end to a second end (e.g., similar to first end 150 and second end 152 described above), and the interior clearance 510 may be closed at both ends of the C-shaped portion 500. In some examples, an entirety of the x-ray tube 502 may be positioned within the interior clearance 510. In other examples, a different amount of the x-ray tube 502 (e.g., at least half of the x-ray tube 502) may be positioned within the interior clearance 510.

In examples in which the C-shaped portion 500 is formed of a composite material (e.g., similar to the example of C-shaped portion 105 described above), the opening 504 may be formed by the composite material without cutting or machining of the composite material. For example, the composite material may comprise carbon fiber fabric, and the opening 504 may be formed by a plurality of layers of the carbon fiber fabric during fabrication (e.g., molding) without cutting or otherwise machining (e.g., drilling, perforating, etc.) the carbon fiber fabric.

The C-shaped portion 500 includes a first pair of grooved flanges comprising a first grooved flange 520 arranged at first sidewall 514 and a second grooved flange 522 arranged at second sidewall 516, as well as a second pair of grooved flanges comprising a third grooved flange 524 arranged at first sidewall 514 opposite to the first grooved flange 520 and a fourth grooved flange 526 arranged at the second sidewall 516 opposite to the second grooved flange 522. In this configuration, the first grooved flange 520 is mirror symmetric to the second grooved flange 522, and the third grooved flange 524 is mirror symmetric to the fourth grooved flange 526. The first grooved flange 520 and second grooved flange 522 are formed by the inner circumferential wall 512, and the third grooved flange 524 and fourth grooved flange 526 are formed by the outer circumferential wall 506. For example, the inner circumferential wall 512 and outer circumferential wall 506 may each be formed of composite material such as carbon fiber fabric. At least one layer of carbon fiber fabric may form together each of the first grooved flange 520, second grooved flange 522, and inner circumferential wall 512, and at least one layer of carbon fiber fabric may form together each of the third grooved flange 524, fourth grooved flange 526, and outer circumferential wall 506. Further, at least one layer of carbon fiber fabric may form together each of the first grooved flange 520, third grooved flange 524, and first sidewall 514, and at least one layer of carbon fiber fabric may form together each of the second grooved flange 522, fourth grooved flange 526, and second sidewall 516. Example carbon fiber layering is shown by FIGS. 8-9 and described further below.

As described above, the x-ray tube 502 may be seated within the interior clearance 510 of the C-shaped portion 500. The interior clearance 510 is formed between the inner circumferential wall 512, outer circumferential wall 506, first sidewall 514, and second sidewall 516, and during conditions in which the x-ray tube 502 is seated within the interior clearance 510 (e.g., seated in face-sharing contact against the outer circumferential wall 506 within the interior clearance 510), at least a portion of the x-ray tube 502 is arranged between the first pair of grooved flanges and the second pair of grooved flanges. For example, the broken lines 508 illustrate a portion of the x-ray tube 502 positioned between the first pair of grooved flanges (e.g., first grooved flange 520 and second grooved flange 522) and the second pair of grooved flanges (e.g., third grooved flange 524 and fourth grooved flange 526) in a direction from the inner circumferential wall 512 to the outer circumferential wall 506. Further, at least a portion of the x-ray tube 502 is shown positioned between the first grooved flange 520 and second grooved flange 522.

Referring to FIG. 6, another view of the C-shaped portion 500 is shown. The view shown by FIG. 5 shows one end of the C-shaped portion 500 (e.g., similar to the second end 152 of C-shaped portion 105 described above), and the view shown by FIG. 6 shows another end of the C-shaped portion 500 (e.g., similar to first end 150 of C-shaped portion 105). For illustrative clarity, the view shown by FIG. 6 does not show the detector (e.g., detector 108 described above) coupled to the C-shaped portion 500.

Each of the grooved flanges (e.g., first grooved flange 520, second grooved flange 522, third grooved flange 524, and fourth grooved flange 526) includes a respective groove configured to engage with a corresponding annular rod. First grooved flange 520 includes first groove 530 configured to engage with first annular rod 600, second grooved flange 522 includes second groove 532 configured to engage with second annular rod 602, third grooved flange 524 includes third groove 534 shaped to engage with third annular rod 604, and fourth grooved flange 526 includes fourth groove 536 shaped to engage with fourth annular rod 606. Each grooved flange and corresponding groove may extend an entire length of the C-shaped portion 500 in some examples. The first annular rod 600 and second annular rod 602 may each have a same radius of curvature as the first grooved flange 520, second grooved flange 522, and inner circumferential wall 512, and the third annular rod 604 and fourth annular rod 606 may each have a same radius of curvature as the third grooved flange 524, fourth grooved flange 526, and outer circumferential wall 506.

As described above, the first grooved flange 520 is mirror symmetric to the second grooved flange 522 and the third grooved flange 524 is mirror symmetric to the fourth grooved flange 526. For example, a shape of the first grooved flange 520 (and first groove 530) may be mirror symmetric to a shape of the second grooved flange 522 (and second groove 532) across axis 700 (shown by FIG. 7), and a shape of the third grooved flange 524 (and third groove 534) may be mirror symmetric to a shape of the fourth grooved flange 526 (and groove 536) across the axis 700, with the axis extending in a direction normal to the inner circumferential wall 512 and outer circumferential wall 506. In some examples, the grooves of the grooved flanges (e.g., first groove 530, second groove 532, etc.) may each have a uniform radius of curvature (e.g., a circular cross-section). In other examples, the grooves may be shaped differently (e.g., having a trapezoidal cross-section, rectangular cross-section, triangular cross-section, etc.). Each grooved flange of the first pair of grooved flanges may extend an entire length of inner circumferential wall 512, and each grooved flange of second pair of grooved flanges may extend an entire length of the outer circumferential wall 506. For example, each grooved flange may extend along an outer perimeter of the C-shaped portion 500 from the first end to the second end of the C-shaped portion 500.

Referring collectively to FIGS. 7-8, the C-shaped portion 500 is shown with the annular rods engaged with respective grooved rollers. FIG. 7 shows a perspective view of the C-shaped portion 500, and FIG. 8 shows a cross-sectional view of portion 780 of the C-shaped portion 500 shown by FIG. 7. The first annular rod 600 and third annular rod 604 are shown engaged with the first groove 530 and third groove 534, respectively. The first annular rod 600 forms an interface between the first groove 530 and first bearing assembly 750 (e.g., a first grooved roller), and the third annular rod 604 forms an interface between the third groove 534 and second bearing assembly 760 (e.g., a second grooved roller). First bearing assembly 750 may include several components similar to second bearing assembly 760, and although second bearing assembly 760 is described herein, it should be noted that a similar configuration may apply to the first bearing assembly 750.

Second bearing assembly 760 includes rolling elements 762 (e.g., ball bearings) disposed within a housing 766. Each rolling element is seated between respective opposing channels 764 of the housing 766 and is maintained between the channels by guides 768. Further, the second bearing assembly 760 includes an outer channel 770 (e.g., a groove) configured to be in face-sharing contact with the third annular rod 604 in order to form the interface with third annular rod 604. In this configuration, the grooved flanges of the C-shaped portion interface with the bearing assemblies via the annular rods in order to rotatably couple the C-arm to the imaging system.

As described above, each of the grooved flanges of the C-shaped portion 500 may be formed from composite material such as carbon fiber (e.g., carbon fiber fabric). As one example, FIG. 8 shows a plurality of layers of carbon fiber fabric forming the first grooved flange 520 and third grooved flange 524. The plurality of layers includes a first exterior layer 702 forming each of a surface of the third groove 534 shaped to engage with third annular rod 604, a portion of the first sidewall 514, and a surface of the first groove 530 shaped to engage with the first annular rod 600. The plurality of layers further includes a second exterior layer 716 forming a portion of the outer circumferential wall 506 along with the third grooved flange 524. Disposed between the first exterior layer 702 and the second exterior layer 716 is a plurality of intermediate layers which may increase a strength of the components formed by the carbon fiber fabric. In the example shown by FIG. 8, the intermediate layers include first intermediate layer 704, second intermediate layer 706, third intermediate layer 708, fourth intermediate layer 710, fifth intermediate layer 712, and sixth intermediate layer 714. In other examples, a different amount of intermediate layers may be included (e.g., ten layers, twenty layers, etc.). Further, in some examples, a thickness and/or arrangement of the intermediate layers may be different compared to the example shown by FIG. 8.

In the configuration shown, the first exterior layer 702 forms the first sidewall 514, first grooved flange 520, and third grooved flange 524 as a unitary, continuous piece without cutting or machining (e.g., the first exterior layer 702 is a unitary, continuous piece, and forms each of the first sidewall 514, first grooved flange 520, and third grooved flange 524 together without cutting or machining such as drilling, etc.). As a result, the first sidewall 514, first grooved flange 520, and third grooved flange 524 may have reduced weight and/or increased strength relative to grooved flanges and sidewalls that are not formed from the carbon fiber fabric. Additionally, although FIG. 8 shows first sidewall 514, first grooved flange 520, and third grooved flange 524, it should be noted that second sidewall 516, second grooved flange 522, and fourth grooved flange 526 may include a similar configuration of carbon fiber layers (e.g., with each of second sidewall 516, second grooved flange 522, and fourth grooved flange 526 formed by a respective exterior layer as a unitary, continuous piece without cutting or machining). It should also be appreciated that the second exterior layer forming third grooved flange 525 may additionally form the outer circumferential wall 506 and fourth grooved flange 526, and the first grooved flange 520, inner circumferential wall 512, and second grooved flange 522 may be similarly formed by a respective exterior layer of carbon fiber fabric.

Referring to FIG. 9, an exploded view of an example construction of a grooved flange of a C-shaped portion of a C-arm is shown. In some examples, the grooved flange may be one of the grooved flanges described above (e.g., third grooved flange 524), and the C-shaped portion may be one of the C-shaped portions described above (e.g., C-shaped portion 105 or C-shaped portion 500). In the example shown by FIG. 9, the example construction includes eight layers of carbon fiber fabric. However, in other examples, the construction may include a different number of layers (e.g., fifteen layers, thirty layers, etc.).

Each of the layers shown by FIG. 9 may be assembled along assembly axis 800 in order to form the grooved flange. The plurality of layers includes a first exterior layer 802 and a second exterior layer 804, similar to the first exterior layer 702 and second exterior layer 716 described above. The plurality of layers further includes a plurality of intermediate layers 806, with the intermediate layers including a first intermediate layer 808, second intermediate layer 810, third intermediate layer 812, fourth intermediate layer 814, fifth intermediate layer 816, and sixth intermediate layer 818, which may be similar to the intermediate layers described above with reference to FIG. 8.

The first exterior layer 802 forms a surface 820 the grooved flange configured to engage with an annular rod, such as the third annular rod 604 described above. The first exterior layer 802 and second exterior layer 804 may each be formed from woven carbon fiber fabric, with a first plurality of carbon fibers of the woven carbon fiber fabric arranged perpendicular to a second plurality of carbon fibers of the woven carbon fiber fabric. In the example shown by FIG. 9, the solid lines through each layer indicate a direction of the carbon fibers of the layer. First exterior layer 802 and second exterior layer 804 may each include carbon fibers woven together in a first direction 822 and a second direction 824, with the second direction 824 perpendicular to the first direction 822, while the intermediate layers may include parallel carbon fibers arranged only in the second direction 824.

Configuring the grooved flange to include exterior layers of carbon fiber with the fibers of each layer arranged in the first direction 822 and the perpendicular, second direction 824 may increase a strength of the grooved flange (e.g., decrease a likelihood of degradation of the exterior surfaces of the grooved flange, such as surface 820). Further, by configuring the intermediate layers of carbon fiber to include only carbon fibers extending in the second direction 824 parallel to a direction of the groove of the grooved flange (e.g., around a perimeter of the C-shaped portion and around a rotational axis of the C-shaped portion, such as rotational axis 164 described above), the strength of the grooved flange may be increased.

In this way, the technical effect of forming the grooved flanges from the layers of carbon fiber material is to increase a strength of the grooved flanges and reduce a load (e.g., weight) of the imaging system. The seated position of the x-ray source within the C-shaped portion may increase a balance of the C-arm, which may reduce a likelihood of undesired vibration of the C-arm (e.g., during isocentric rotation of the C-shaped portion). Further, the seated position of the x-ray source and the isocentric rotation of the C-arm provide an increased amount of space between the x-ray source and the detector to accommodate larger patients and increase an ease of use of the imaging system (e.g., by providing a larger imaging area).

FIGS. 5-8 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, the term "approximately" is construed to mean plus or minus five percent of the range unless otherwise specified.

In one embodiment, an imaging system comprises: a C-arm including an inner circumferential wall forming a first pair of grooved flanges and the outer circumferential wall forming a second pair of grooved flanges, where each of the first pair of grooved flanges and second pair of grooved flanges comprises a composite material. In a first example of the imaging system, the imaging system further comprises an interior clearance formed between the inner circumferential wall and outer circumferential wall, the interior clearance shaped to house an x-ray source between the first pair of grooved flanges and the second pair of grooved flanges. A second example of the imaging system optionally includes the first example, and further includes wherein the composite material comprises carbon fiber. A third example of the imaging system optionally includes one or both of the first and second examples, and further includes wherein the carbon fiber includes a first exterior layer, a second exterior layer, and one or more intermediate layers, where each of the first exterior layer and second exterior layer include carbon fibers woven perpendicular to each other, and where the one or more intermediate layers include carbon fibers arranged only parallel to each other. A fourth example of the imaging system optionally includes one or more or each of the first through third examples, and further includes wherein the composite material includes a first layer forming each grooved flange of the first pair of grooved flanges. A fifth example of the imaging system optionally includes one or more or each of the first through fourth examples, and further includes wherein the composite material includes a first layer forming both of a first grooved flange of the first pair of grooved flanges and a second grooved flange of the second pair of grooved flanges. A sixth example of the imaging system optionally includes one or more or each of the first through fifth examples, and further includes a first sidewall and an opposing, second sidewall joining the inner circumferential wall to the outer circumferential wall. A seventh example of the imaging system optionally includes one or more or each of the first through sixth examples, and further includes wherein the first pair of grooved flanges comprises a first grooved flanged arranged at the first sidewall and a second grooved flange arranged at the second sidewall, and the second pair of grooved flanges comprises a third grooved flange arranged at the first sidewall opposite the first grooved flange and a fourth grooved flange arranged at the second sidewall opposite the second grooved flange. An eighth example of the imaging system optionally includes one or more or each of the first through seventh examples, and further includes wherein the first sidewall, second sidewall, inner circumferential wall, and outer circumferential wall are formed from the composite material. A ninth example of the imaging system optionally includes one or more or each of the first through eighth examples, and further includes wherein the composite material comprises a plurality of layers of carbon fiber, and wherein a first layer of the plurality of layers forms the first sidewall, the first grooved flange, and the third grooved flange, and wherein a second layer of the plurality of layers forms the second sidewall, the second grooved flange, and the fourth grooved flange. A tenth example of the imaging system optionally includes one or more or each of the first through ninth examples, and further includes wherein the first layer is a unitary, continuous piece forming the first sidewall, first grooved flange, and third grooved flange without cutting or machining, and wherein the second layer is a unitary, continuous piece forming the second sidewall, second grooved flange, and fourth grooved flange without cutting or machining.

In another embodiment, an imaging system comprises: a base unit; a C-arm coupled to the base unit and including an x-ray source and detector positioned on opposite ends of a C-shaped portion of the C-arm, where the C-shaped portion includes an inner circumferential wall and an outer circumferential wall separated by an interior clearance, the inner circumferential wall forming a first pair of grooved flanges and the outer circumferential wall forming a second pair of grooved flanges; and an opening formed in the inner circumferential wall shaped to receive a casing of the x-ray source between opposing grooved flanges of the first pair of grooved flanges, with the x-ray source seated within the interior clearance. In a first example of the imaging system, each grooved flange of the first pair of grooved flanges and each grooved flange of the second pair of grooved flanges is formed from a plurality of layers of carbon fiber, with the first pair of grooved flanges and second pair of grooved flanges coupling the C-arm to the base unit. A second example of the imaging system optionally includes the first example, and further includes a first sidewall and a second sidewall joining the inner circumferential wall and outer circumferential wall, where the interior clearance is formed between the first sidewall, second sidewall, inner circumferential wall, and outer circumferential wall. A third example of the imaging system optionally includes one or both of the first and second examples, and further includes wherein the x-ray source comprises an x-ray tube seated against the outer circumferential wall. A fourth example of the imaging system optionally includes one or more or each of the first through third examples, and further includes wherein the first pair of grooved flanges includes a first grooved flange and a second grooved flange, the second pair of grooved flanges includes a third grooved flange and a fourth grooved flange, the first grooved flange is mirror symmetric to the second grooved flange, the third grooved flange is mirror symmetric to the fourth grooved flange, and where each grooved flange comprises a respective groove having a circular, trapezoidal, rectangular, or trigonal shape. A fifth example of the imaging system optionally includes one or more or each of the first through fourth examples, and further includes wherein each grooved flange of the first pair of grooved flanges extends an entire length of the inner circumferential wall, and each grooved flange of second pair of grooved flanges extends an entire length of the outer circumferential wall.

In one embodiment, a C-arm for a medical imaging system comprises: a C-shaped portion adapted to rotate isocentrically around a rotational axis centered between a first end and an opposing, second end of the C-shaped portion, where the rotational axis is closer to a detector surface at the first end than an x-ray source seated within the second end; and a grooved flange extending along an outer perimeter of the C-shaped portion from the first end to the second end and shaped to engage with an annular rod, where the grooved flange is formed of a composite material. In a first example of the C-arm, the composite material comprises carbon fiber, and the annular rod forms an interface between the grooved flange and a bearing assembly of the medical imaging system. A second example of the C-arm optionally includes the first example, and further includes wherein a surface of the grooved flange configured to engage with the annular rod is formed from woven carbon fiber, with a first plurality of carbon fibers of the woven carbon fiber arranged perpendicular to a second plurality of carbon fibers of the woven carbon fiber.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging system, comprising:
a C-arm including an inner circumferential wall forming a first pair of grooved flanges and the outer circumferential wall forming a second pair of grooved flanges, where each of the first pair of grooved flanges and second pair of grooved flanges comprises a composite material.

2. The imaging system of claim 1, further comprising an interior clearance formed between the inner circumferential wall and outer circumferential wall, the interior clearance shaped to house an x-ray source between the first pair of grooved flanges and the second pair of grooved flanges.

3. The imaging system of claim 1, wherein the composite material comprises carbon fiber.

4. The imaging system of claim 3, wherein the carbon fiber includes a first exterior layer, a second exterior layer, and one or more intermediate layers, where each of the first exterior layer and second exterior layer include carbon fibers woven perpendicular to each other, and where the one or more intermediate layers include carbon fibers arranged only parallel to each other.

5. The imaging system of claim 1, wherein the composite material includes a first layer forming each grooved flange of the first pair of grooved flanges.

6. The imaging system of claim 1, wherein the composite material includes a first layer forming both of a first grooved flange of the first pair of grooved flanges and a second grooved flange of the second pair of grooved flanges.

7. The imaging system of claim 1, further comprising a first sidewall and an opposing, second sidewall joining the inner circumferential wall to the outer circumferential wall.

8. The imaging system of claim 7, wherein the first pair of grooved flanges comprises a first grooved flanged arranged at the first sidewall and a second grooved flange arranged at the second sidewall, and the second pair of grooved flanges comprises a third grooved flange arranged at the first sidewall opposite the first grooved flange and a fourth grooved flange arranged at the second sidewall opposite the second grooved flange.

9. The imaging system of claim 8, wherein the first sidewall, second sidewall, inner circumferential wall, and outer circumferential wall are formed from the composite material.

10. The imaging system of claim 9, wherein the composite material comprises a plurality of layers of carbon fiber, and wherein a first layer of the plurality of layers forms the first sidewall, the first grooved flange, and the third grooved flange, and wherein a second layer of the plurality of layers forms the second sidewall, the second grooved flange, and the fourth grooved flange.

11. The imaging system of claim 10, wherein the first layer is a unitary, continuous piece forming the first sidewall, first grooved flange, and third grooved flange without cutting or machining, and wherein the second layer is a unitary, continuous piece forming the second sidewall, second grooved flange, and fourth grooved flange without cutting or machining.

12. An imaging system, comprising:
a base unit;
a C-arm coupled to the base unit and including an x-ray source and detector positioned on opposite ends of a C-shaped portion of the C-arm, where the C-shaped portion includes an inner circumferential wall and an outer circumferential wall separated by an interior clearance, the inner circumferential wall forming a first pair of grooved flanges and the outer circumferential wall forming a second pair of grooved flanges; and
an opening formed in the inner circumferential wall shaped to receive a casing of the x-ray source between opposing grooved flanges of the first pair of grooved flanges, with the x-ray source seated within the interior clearance; wherein each grooved flange of the first pair of grooved flanges and each grooved flange of the second pair of grooved flanges is formed from a plurality of layers of carbon fiber, with the first pair of grooved flanges and second pair of grooved flanges coupling the C-arm to the base unit.

13. The imaging system of claim 12, further comprising a first sidewall and a second sidewall joining the inner circumferential wall and outer circumferential wall, where the interior clearance is formed between the first sidewall, second sidewall, inner circumferential wall, and outer circumferential wall.

14. The imaging system of claim 12, wherein the x-ray source comprises an x-ray tube seated against the outer circumferential wall.

15. The imaging system of claim 12, wherein the first pair of grooved flanges includes a first grooved flange and a second grooved flange, the second pair of grooved flanges includes a third grooved flange and a fourth grooved flange, the first grooved flange is mirror symmetric to the second grooved flange, the third grooved flange is mirror symmetric to the fourth grooved flange, and where each grooved flange comprises a respective groove having a circular, trapezoidal, rectangular, or trigonal shape.

16. The imaging system of claim 12, wherein each grooved flange of the first pair of grooved flanges extends an entire length of the inner circumferential wall, and each grooved flange of second pair of grooved flanges extends an entire length of the outer circumferential wall.

17. A C-arm for a medical imaging system, comprising:
a C-shaped portion to rotate isocentrically around a rotational axis centered between a first end and an opposing, second end of the C-shaped portion, where the rotational axis is closer to a detector surface at the first end than an x-ray source seated within the second end; and
a grooved flange extending along an outer perimeter of the C-shaped portion from the first end to the second end and shaped to engage with an annular rod, where the grooved flange is formed of a composite material.

18. The C-arm of claim 17, wherein the composite material comprises carbon fiber, and the annular rod forms an interface between the grooved flange and a bearing assembly of the medical imaging system.

19. The C-arm of claim 17, wherein a surface of the grooved flange configured to engage with the annular rod is formed from woven carbon fiber, with a first plurality of carbon fibers of the woven carbon fiber arranged perpendicular to a second plurality of carbon fibers of the woven carbon fiber.

* * * * *